United States Patent [19]

Saito et al.

[11] 4,387,095
[45] Jun. 7, 1983

[54] COMBATING PESTS WITH O-ALKYL-S-ALKYL-S-ACYLOXYETHYL-PHOSPHORODITHIOLATES

[75] Inventors: Junichi Saito; Akio Kudamatsu; Kozo Shiokawa; Shinichi Tsuboi, all of Tokyo, Japan

[73] Assignee: Nihon Tokushu Noyaku Seizo K.K., Tokyo, Japan

[21] Appl. No.: 295,983

[22] Filed: Aug. 25, 1981

[30] Foreign Application Priority Data

Sep. 1, 1980 [JP] Japan .................................. 55-119854

[51] Int. Cl.³ ........................ C07F 9/165; A01N 57/12
[52] U.S. Cl. ..................................... 424/211; 260/938; 260/952; 424/212
[58] Field of Search ................. 260/938, 952; 424/211, 424/212

[56] References Cited

FOREIGN PATENT DOCUMENTS 2628410 1/1978 Fed. Rep. of Germany .
52-9738 3/1977 Japan .
948783 2/1964 United Kingdom .

OTHER PUBLICATIONS

Agricultural Chemistry, p. 4, vol. 77, No. 12, Derwent Abstract of Japanese 70 09738.

*Primary Examiner*—Anton H. Sutto
*Attorney, Agent, or Firm*—Sprung, Horn, Kramer & Woods

[57] ABSTRACT

O-Alkyl-S-alkyl-S-acyloxyethyl-phosphorodithioldates of the formula

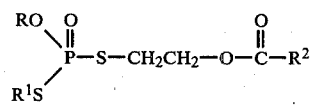

wherein
R is an alkyl group having 1 to 6 carbon atoms,
$R^1$ is an alkyl group having 1 to 6 carbon atoms or an alkoxyethyl group having 1 to 6 carbon atoms in the alkyl part, and
$R^2$ is an alkoxy group having 1 to 6 carbon atoms, an amino group mono- or di-substituted by an alkyl group having 1 to 6 carbon atoms, an unsubstituted anilino group, or an anilino group substituted at the N-position by an alkyl group having 1 to 6 carbon atoms, which possess pesticidal, e.g. insecticidal, acaricidal and nematicidal, properties.

9 Claims, No Drawings

COMBATING PESTS WITH O-ALKYL-S-ALKYL-S-ACYLOXYETHYL-PHOSPHORODITHIOLATES

The present invention relates to certain new organophosphates to a process for their production and to their use as agents for combating pests, especially as insecticides, acaricides and nematocides.

It has already been disclosed in Japanese Published Patent Application No. 9738/77 that a compound of the general formula

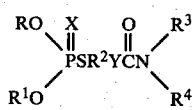

wherein

R and $R^1$ each represents a lower alkyl group or a cyclohexyl group, $R^2$ represents a linear or branched lower alkylene group having at least 2 carbon atoms, $R^3$ is a lower alkyl group $R^4$ represents a hydrogen atom or a lower alkyl group, and X and Y each represents an oxygen or sulfur atom, has insecticidal, acaricidal and fungicidal activities can be used in agriculture and horticulture.

Likewise, it is known from DE-OS (German Published Specification) No. 2628410 that a compound of the general formula

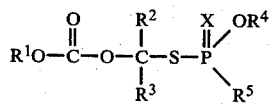

wherein $R^1$ represents an alkyl group having 1 to 6 carbon atoms, $R^2$ and $R^3$ each represents a hydrogen atom or an alkyl group having 1 to 3 carbon atoms, $R^4$ represents an alkyl group having 1 to 6 carbon atoms, $R^5$ represents an alkoxy group having 1 to 6 carbon atoms, an alkylthio group, an alkenylthio group, an alkynylthio group, an alkoxyalkylthio group, an alkylthioalkylthio group, a benzylthio group, an alkyl group having 1 to 3 carbon atoms, an optionally substituted phenyl group, an amino group, an alkylamino or dialkylamino group having 1 to 5 carbon atoms, and X represents an oxygen or sulfur atom, has insecticidal, acaricidal and nematocidal activities.

The present invention now provides, as new compounds, organophosphates of the general formula:

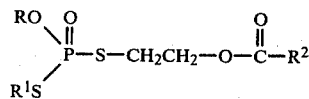

wherein

R represents an alkyl group having 1 to 6 carbon atoms, $R^1$ represents an alkyl group having 1 to 6 carbon atoms or an alkoxyethyl group having 1 to 6 carbon atoms in the alkyl part, and $R^2$ represents an alkoxy group having 1 to 6 carbon atoms, an amino group mono- or di-substituted by an alkyl group having 1 to 6 carbon atoms, an unsubstituted anilino group, or an anilino group substituted at the N-position by an alkyl group having 1 to 6 carbon atoms.

The present invention also provides a process for preparing an organophosphate of the formula (I), in which a compound of the general formula

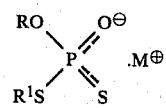

wherein

R and $R^1$ are as defined hereinabove, and

M represents an alkali metal atom or an ammonium group, is reacted with a compound of the general formula

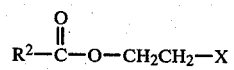

wherein $R^2$ is as defined above, and

X represents a halogen atom.

The organophosphates of the present invention have outstandingly excellent biological activities and in particular exhibit excellent insecticidal, acaricidal and nematocidal effects against a broad range of pests as well as resistant pests. The structurally most closely analogous compounds of the prior art, namely compounds of general formula (V), do not exhibit the same high biological activities as do the compounds of this invention. Accordingly the compounds of the present invention represent a very great technical advance which could not have been expected.

The process according to the present invention may be represented by the following equation:

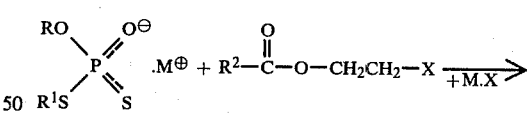

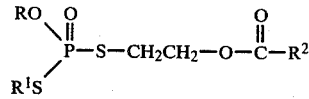

(wherein R, $R^1$, $R^2$, M and X are as defined hereinabove).

Preferred compounds of the present invention and intermediates for their production are those in which R represents an alkyl radical selected from methyl, ethyl, n-(or iso-)propyl, n-(iso, sec-, or tert-)butyl, amyl and hexyl, $R^1$ represents an alkyl group independently selected from those mentioned above, or is an alkoxyethyl group, the alkyl part of which is independently selected from those mentioned above, and $R^2$ represents an alkoxy group, the alkyl part of which is independently selected from those mentioned above, an amino group which is mono- or di-substituted by an alkyl group independently selected from those mentioned above, an unsubstituted anilino group, or an anilino group substituted at the N-position by an alkyl group independently selected from those mentioned above. Particularly preferred compounds of the present invention are those in which R represents an ethyl group and $R^1$ represents a propyl, sec-butyl or 2-ethoxyethyl group.

The process for the preparation of the compounds of the present invention has been disclosed above. Examples of starting materials for the process of the present invention specifically include potassium O-ethyl S-propylphosphorodithioate, potassium O-ethyl S-sec-butylphosphorodithioate, and potassium O-ethyl S-(2-ethoxyethyl)phosphorodithioate, and the corresponding sodium and ammonium salts.

Specific examples of the compound of general formula (III) for use as a starting material in the process of the present invention include 2-bromoethyl methylcarbonate, 2-bromoethyl ethylcarbonate, 2-bromoethyl N-methylcarbamate, 2-bromoethyl N,N-dimethylcarbamate, 2-bromoethyl N,N-diethylcarbamate, 2-bromoethyl N-phenylcarbamate, and 2-bromoethyl N-methyl N-phenylcarbamate. Instead of the bromo-substituted products, the corresponding chloro-substituted products may also be mentioned.

If potassium O-ethyl-S-propylphosphorodithioate and 2-bromoethyl N,N-dimethylcarbamate are used as starting materials, the process of the present invention is illustrated by the following equation:

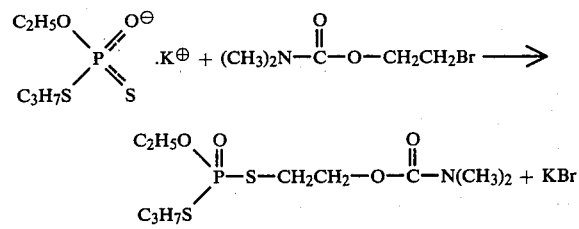

The process of the present invention is preferably performed using a solvent or a diluent. For this purpose, any inert solvent or diluent may be used.

Examples of such solvents or diluents include water; aliphatic, alicyclic and aromatic hydrocarbons and chlorinated hydrocarbons (such as hexane, cyclohexane, petroleum ether, ligroin, benzene, toluene, xylene, methylene chloride, chloroform, carbon tetrachloride, ethylene chloride, trichloroethylene and chlorobenzene); ethers (such as diethyl ether, methyl ethyl ether, di-iso-propyl ether, dibutyl ether, propylene oxide, dioxane and tetrahydrofuran); ketones (such as acetone, methyl ethyl ketone, methyl isopropyl ketone, and methyl isobutyl ketone); nitriles (such as acetonitrile, propionitrile and acrylonitrile); alcohols (such as methanol, ethanol, isopropanol, butanol and ethylene glycol); esters (such as ethyl acetate and amyl acetate); acid amides (such as dimethylformamide and dimethylacetamide); sulfones and sulfoxides (such as dimethyl sulfoxide and sulfolane); and bases (such as pyridine).

The process of this invention can be carried out over a wide temperature range. Generally, it is carried out at a temperature between −20° C. and the boiling point of the reaction mixture, preferably between 0° and 100° C. Preferably, the reaction is carried out under atmospheric pressure, but it is possible to operate under elevated or reduced pressure.

The compounds of this invention have excellent effects, and exhibit an accurate control effect against pests, especially against insects, mites, and nematodes, without any phytotoxicity to crops. The compounds of this invention can be used to control a broad range of pests, in particular sucking insects, biting insects and other pests parasitic on plants, grain pests and pests injurious to man's health, and can be used for control and eradication of these pests. The abovementioned pests include:

From the order of Coleoptera, for example, *Lissorhoptrus oryzophilus, Collosobruchus chinensis, Sitophilus zeamais, Tribolium castaneum, Epilachna vigintiocsomaculata, Agriotes fuscicollis, Anomala rufocuprea, Leptinotorsa decemlineata,* Diabrotica spp., *Monochamus altarnatus,* and *Lyctus brunneus;*

From the order of Lepidoptera, for example, *Lymantria dispar, Malacosoma neustria, Pieris rapae, Spodoptera litura, Mamestra brassicae, Chilo suppressalis, Phrausta nubilalis, Ephestia cautella, Adoxophyes orana, Carpocapsa pomonella, Galleria mellonella,* and *Phyllocnistis citrella.*

From the order of Hemiptera, for example, *Nephotettix cincticeps, Nilaparvata lugens, Pseudococcus comstocki, Unaspis yanonensis, Myzus persicae, Aphis pomi, Rhopalosiphum pseudobrassicae, Stephanitis nashi,* Nezara spp., *Cimex lectularius, Trialourodes vaporariorum,* and Psylla spp.;

From the order of Orthoptera, for example, *Blatella germanica, Periplaneta americana, Gryllotalpa africana,* and *Locusta migratoria migratoriodes:*

From the order of Isoptera, for example, *Leucotermes speratus,* and *Coptotermes formosanus;*

From the order of Diptera, for example, *Musca domestica, Aedes aegypti, Hylemyia platura, Culex pipiens, Anophetes sinensis,* and *Culex tritaeniorhynchus;*

From the order of the Acarina, for example, *Tetranychus telarius, Panonychus citri, Aculus pelekassi* and Torronomus spp.

The plant-parasitic nematodes include *Meloidogyne incognita, Aphelenchoides besseyi, Heterodera glycines,* Pratylenchus spp.

In the field of veterinary medicines, the novel compounds of this invention are effectively used against various animal parasites (endoparasites and ectoparasites), such as ticks, insects and parasitic worms.

Examples of ticks are Oranithodoros spp., Ixodes spp. and Boophilus spp.

Examples of insects are Gastrophilus spp., Stomoxys spp., Trichodectes spp., Rhodnius spp., and *Ctenocephalides canis.*

When the compound of this invention is used as an insecticidal, acaricidal or nematocidal agent, it may be used after diluting it directly with water, or after formulating it into various forms as is generally practiced in the field of manufacturing agricultural chemicals using agriculturally acceptable adjuvants. These various formulations can be used directly or after being diluted to the desired concentration with water prior to actual use.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents.

In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

In actual use, the suitable amount of the active compound in the aforesaid various preparations and ready-to-use preparations is generally 0.0001 to 20% by weight, preferably 0.005 to 10% by weight.

The content of the active ingredient may be varied depending upon the form of the formulated compound, the method, purpose, time and place of application, the state of occurrence of pests, especially insects, acarids and nematodes.

If further required, the compound of this invention may be used in combination with another agricultural chemical, for example an insecticide, fungicide, acaricide, nematocide, antiviral agent, herbicide, plant growth regulator or attractant (such as organophosphate compounds, carbamate compounds, dithio (or thiol) carbamate compounds, organo-chlorine compounds, dinitro compounds, organosulfur compounds or organometallic compounds, antibiotics, substituted diphenyl ether compounds, urea compounds, and triazine compounds), and/or fertilizers.

Various formulations or ready-to-use preparations containing the active ingredient of this invention may be applied by methods usually practised generally in the field of producing agricultural chemicals, for example spraying (e.g., liquid spraying, misting, atomizing, dusting, granule spraying, water surface application, or pouring), fumigation, soil application (for example, mixing, sprinkling, vaporing, or irrigation), surface application (e.g., coating, banding, dust coating, or covering), dipping and baiting. They may also be applied by the so-called ultralow-volume method, in which the active ingredient may be included in a concentration of 100%.

The rate of application of the active compound per unit area of agriculture is generally about 0.03 to 10 kg, preferably 0.3 to 6 kg, per hectare as the active ingredient. In special cases, however, the rate of application may exceed the specified range, or may be below the lower limit, and this is necessary at times.

The present invention also provides pesticidal compositions containing as active ingredient a compound of the present invention in admixture with a solid or liquefied gaseous diluent or carrier or in admixture with a liquid diluent or carrier containing a surface-active agent.

The present invention also provides a method of combating pests (in particular nematodes, or arthropods, especially insects or acarids) which comprises applying to the pests or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

The present invention further provides domesticated animals whenever freed or protected from parasites by the application to said animals of a compound according to the present invention, in admixture with a diluent or carrier.

The process for the preparation of compounds according to the present invention is illustrated in the following examples:

EXAMPLE 1

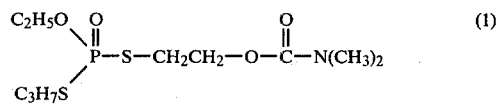

Potassium O-ethyl S-propylphosphorodithioate (26.2 g) was dissolved in 120 ml of methyl ethyl ketone, and 19.6 g of 2-bromoethyl N,N-dimethylcarbamate was added. The solution was heated at 70° to 75° for 4 hours with stirring. After the reaction, the methyl ethyl ketone was distilled off under reduced pressure, and toluene was added to the residue. The mixture was washed with water and a 1% aqueous solution of sodium hydroxide. The toluene was distilled off from the toluene layer to leave 24.0 g of the desired O-ethyl-S-2-(dimethylcarbamoyloxy)-ethyl-S-propylphosphorodithiolate as a colorless oil $n_D^{20} = 1.5042$.

The compounds of the present invention shown in Table 1 were synthesized by substantially the same method as that described above.

TABLE 1

$$\begin{array}{c} RO \quad O \\ \diagdown \parallel \\ P-S-CH_2CH_2-O-\overset{O}{\overset{\parallel}{C}}-R^2 \\ \diagup \\ R^1S \end{array}$$

| Compound No. | R | R$^1$ | R$^2$ | Physical constant |
|---|---|---|---|---|
| 2 | —C$_2$H$_5$ | —C$_3$H$_7$ | —OCH$_3$ | $n_D^{20}$ 1.4994 |
| 3 | —C$_2$H$_5$ | —C$_3$H$_7$ | —OC$_2$H$_5$ | $n_D^{20}$ 1.4954 |
| 4 | —C$_2$H$_5$ | —C$_3$H$_7$ | —NHCH$_3$ | $n_D^{20}$ 1.5145 |
| 5 | —C$_2$H$_5$ | —C$_3$H$_7$ | —N(C$_2$H$_5$)$_2$ | $n_D^{20}$ 1.5008 |
| 6 | —C$_2$H$_5$ | —C$_3$H$_7$ | 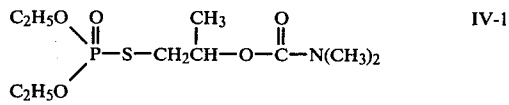 | $n_D^{20}$ 1.5591 |
| 7 | —C$_2$H$_5$ | —C$_3$H$_7$ | 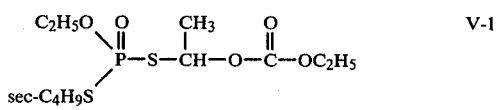 | $n_D^{20}$ 1.5450 |
| 8 | —C$_2$H$_5$ | —C$_4$H$_9$—sec | —OCH$_3$ | $n_D^{20}$ 1.4980 |
| 9 | —C$_2$H$_5$ | —C$_4$H$_9$—sec | —N(C$_2$H$_5$)$_2$ | $n_D^{20}$ 1.4993 |
| 10 | —C$_2$H$_5$ | —CH$_2$CH$_2$OC$_2$H$_5$ | —OCH$_3$ | $n_D^{20}$ 1.5000 |
| 11 | —C$_2$H$_5$ | —CH$_2$CH$_2$OC$_2$H$_5$ | —N(C$_2$H$_5$)$_2$ | $n_D^{20}$ 1.5005 |

The compositions according to the invention and the pesticidal activity of the present compounds are illustrated by the following examples, in which "parts" are parts by weight.

In these examples, the compounds according to the present invention are each identified by the number given in brackets) from Example 1 and Table 1 hereinabove:

The known comparison compounds are identified as follows:

$$\begin{array}{c} C_2H_5O \quad O \quad\quad CH_3 \quad O \\ \diagdown \parallel \quad\quad\quad\quad | \quad\quad \parallel \\ P-S-CH_2CH-O-C-N(CH_3)_2 \\ \diagup \\ C_2H_5O \end{array} \quad \text{IV-1}$$

(a compound described in Japanese Published Patent Application No. 9738/77)

$$\begin{array}{c} C_2H_5O \quad O \quad\quad CH_3 \quad O \\ \diagdown \parallel \quad\quad\quad\quad | \quad\quad \parallel \\ P-S-CH-O-C-OC_2H_5 \\ \diagup \\ sec\text{-}C_4H_9S \end{array} \quad \text{V-1}$$

(a compound described in DE-OS 2628410)

$$\begin{array}{c} C_2H_5O \quad O \quad\quad\quad\quad O \\ \diagdown \parallel \quad\quad\quad\quad\quad\quad \parallel \\ P-S-CH_2-O-C-OCH_3 \\ \diagup \\ C_3H_7S \end{array} \quad \text{V-2}$$

(a compound described in the abovementioned DE-OS)

EXAMPLE 2

Fifteen parts of compound (1), 80 parts of a 1:5 mixture of white carbon (a fine powder of hydrous amorphous silicon oxide) and powdery clay, 2 parts of sodium alkylbenzenesulfonate and 3 parts of a sodium alkylnaphthalenesulfonate/formaldehyde condensate were pulverized and mixed to form a wettable powder. The wettable powder was diluted with water, and applied by spraying.

EXAMPLE 3 (EMULSIFIABLE CONCENTRATE)

Thirty parts of compound (2), 55 parts of xylens, 8 parts of polyoxyethylene alkylphenyl ether and 7 parts of calcium alkylbenzenesulfonate were mixed with stirring to form an emulsifiable concentrate. It was diluted with water, and applied by spraying.

EXAMPLE 4

Two parts of compound (3) and 98 parts of powdery clay were pulverized and mixed to form a dust. It was applied by spraying.

EXAMPLE 5

Compound (4) (1.5 parts), 0.5 part of isopropyl hydrogen phosphate (PAP) and 98 parts of powdery clay were pulverized and mixed to form a dust. It was applied by spraying.

EXAMPLE 6

Water (25 parts) was added to a mixture of 10 parts of compound (5), 30 parts of bentonite (montmorillonite), 58 parts of talc and 2 parts of ligninsulfonate, and they were well kneaded. The kneaded mixture was granulated by an extruder-type granulator to form granules having a size of 10 to 40 mesh. The granules were dried at 40° to 50° C. The resulting granules were applied by spraying.

EXAMPLE 7

Clay mineral particles having a particle size distribution in the range of 0.2 to 2 mm (95 parts) were put into a rotary mixer, and with rotation, 5 parts of compound (6) (oily form) were sprayed onto the clay mineral particles to permit uniform absorption and thereby to form granules. The granules were applied by spraying.

EXAMPLE 8

Compound (7) (0.5 part) and 99.5 parts of kerosene were mixed with stirring to form an oil preparation. It was applied by spraying.

EXAMPLE 9

Test on larvae of Spodoptera litura:

| Preparation of a test chemical: | |
|---|---|
| Solvent | xylene, 3 parts by weight. |
| Emulsifier | polyoxyethylene alkylphenylether, 1 part by weight. |

One part by weight of each of the active compounds was mixed with the above amount of the solvent containing the above amount of the emulsifier, and the mixture was diluted with water to a predetermined concentration to form a suitable preparation of the active compound. Test method:

Sweet potato leaves were dipped in an aqueous dilution, in a predetermined concentration, of the active compound. After air-drying the aqueous dilution applied, the leaves were placed in a Petri dish 9 cm in diameter. Then, 10 third instar larvae of spodoptera released into the Petri dish. The dish was placed in a constant-temperature chamber at 28° C. Twenty-four hours later, the number of dead larvae was examined, and the kill ratio was calculated. The results are shown in Table 2.

TABLE 2

| Compound No. | Concentration of the active ingredient (%) | Kill ratio (%) |
| --- | --- | --- |
| (1) | 0.03 | 100 |
| (2) | " | 100 |
| (4) | " | 100 |
| (5) | " | 100 |
| (6) | " | 100 |
| (7) | " | 100 |
| (10) | " | 100 |
| (11) | " | 100 |
| Comparisons | | |
| IV-1 | 0.03 | 0 |
| V-1 | " | 50 |
| V-2 | " | 70 |

EXAMPLE 10

Test on Callosobruchus chinensis:

A filter paper was spread in a Petri dish having a diameter of 9 cm. One milliliter of a water dilution in a predetermined concentration of each of the active compounds, which was prepared as in Example 9, was placed in the dish. Twenty individuals of Callosobruchus chinensis were placed in the Petri dish, and the dish was allowed to stand in a constant-temperature chamber at 28° C. Twenty-four hours later, the number of dead insects was examined, and the kill ratio was examined.

The results are shown in Table 3.

TABLE 3

| Compound No. | Concentration of the active ingredient (%) | Kill ratio (%) |
| --- | --- | --- |
| (1) | 0.01 | 100 |
| (2) | " | 100 |
| (3) | " | 100 |
| (4) | " | 100 |
| (5) | " | 100 |
| (6) | " | 100 |
| (7) | " | 100 |
| (8) | " | 100 |
| (9) | " | 100 |
| (10) | " | 100 |
| (11) | " | 100 |
| Comparisons | | |
| IV-1 | 0.01 | 0 |
| V-1 | " | 60 |
| V-2 | " | 20 |

EXAMPLE 11

Test on Nephotettix cincticeps having resistance to organophosphorus preparations:
Test method:
Rice plants each about 10 cm in height were planted in pots each 12 cm in diameter. To the rice plants was applied an aqueous dilution, in a predetermined concentration, of each of the active compounds prepared as in Example 9 at a rate of 10 ml per pot. After drying the applied dilution, the pots were each capped with a wire gauze 7 cm in diameter and 14 cm in height, and 30 female imagoes of Nephotettix cincticeps having resistance to organophosphorus agents were released. The pots were then placed in a constant-temperature chamber. Twenty-four hours later, the number of dead insects were examined, and the kill ratio was calculated. The results are shown in Table 4.

TABLE 4

| Compound No. | Concentration of the active ingredient (%) | Kill ratio (%) |
| --- | --- | --- |
| (1) | 0.005 | 100 |
| (2) | " | 100 |
| (3) | " | 100 |
| (4) | " | 100 |
| (5) | " | 100 |
| (7) | " | 100 |
| (8) | " | 100 |
| (9) | " | 100 |
| (10) | " | 100 |
| (11) | " | 100 |
| Comparisons | | |
| IV-1 | 0.005 | 0 |
| V-1 | " | 10 |
| V-2 | " | 50 |

EXAMPLE 12

Test on Tetranychus telarius (spray test) Test method:

50 to 100 images of Tetranychus telarius were attached to the leaves of dicotyledonous, two-leaf stage kidney beans cultivated in pots each 6 cm in diameter. Two days later, an aqueous dilution in a predetermined concentration of each of the active compounds formulated in the same way as in Example A was sprayed at a rate of 40 ml per pot. Then, the pots were put in a greenhouse. Ten days later, the control effect was evaluated and expressed by the following control ratings.

| 3 | 0% survival |
| --- | --- |
| 2 | more than 0% but less than 5% survival based on the untreated imagoes |
| 1 | 5-50% survival based on the untreated imagoes |
| 0 | more than 50% survival based on the untreated imagoes |

The results are shown in Table 5.

TABLE 5

| Compound No. | Concentration of the active ingredient (%) | Control rating |
| --- | --- | --- |
| (1) | 0.01 | 3 |
| (2) | " | 3 |
| (3) | " | 3 |
| (8) | " | 3 |
| (9) | " | 3 |
| (10) | " | 3 |
| (11) | " | 3 |
| Comparisons | | |
| IV-1 | 0.03 | 0 |
| V-1 | 0.01 | 0 |
| V-2 | " | 1 |

EXAMPLE 13

Test on Blatella germanica:
Test Method:

A filter paper was spread in a Petri dish having a diameter of 9 cm. One milliliter of a water dilution in a predetermined concentration of each of the active compounds, which was prepared as in Example 9, was peaced in the dish. Ten imagoes of Blatella germanica were placed into it. The Petri dish was placed in a constant-temperature chamber at 28° C. Twenty-four hours later, the number of dead insects was examined, and the kill ratio was calculated. The results are shown in Table 6.

TABLE 6

| Compound No. | Concentration of the active ingredient (%) | Kill ratio (%) |
|---|---|---|
| (1) | 0.05 | 100 |
| (2) | " | 100 |
| (3) | " | 100 |
| (4) | " | 100 |
| (5) | " | 100 |
| (6) | " | 100 |
| (7) | " | 100 |
| (8) | " | 100 |
| (9) | " | 100 |
| (10) | " | 100 |
| (11) | " | 100 |
| Comparisons | | |
| IV-1 | 0.05 | 20 |
| V-1 | " | 35 |
| V-2 | " | 70 |

EXAMPLE 14

Test on the larvae of Culex tritaneniorhynchus:
Test method:
In a high-skirted Petri dish with a diameter of 9 cm was placed 100 ml of a water dilution in a predetermined concentration of each of the active compounds which was prepared as in Example 9. Twenty-five fourth-instar larvae of Culex tritaeniorhynchus were released into the dish, and the dish was put into a constant-temperature chamber at 27° C. Twenty-four hours later, the number of dead insects was examined, and the kill ratio was calculated. The results are shown in Table 7.

TABLE 7

| Compound No. | Concentration of the active ingredient (ppm) | Kill ratio (%) |
|---|---|---|
| (2) | 0.1 | 100 |
| (3) | " | 100 |
| (6) | " | 100 |
| (7) | " | 100 |
| (8) | " | 100 |
| (9) | " | 100 |
| (10) | " | 100 |
| (11) | " | 100 |
| Comparison | | |
| IV-1 | 0.1 | 0 |
| V-1 | " | 20 |
| V-2 | " | 35 |

EXAMPLE 16

Test on Meloidogyne incognita
Preparation of a test chemical:
A test chemical was prepared by pulverizing and mixing 2 parts of each of the active compounds and 98 parts of talc.
Test method:
The active compound formulated as above was added to the soil infested by Meloidogyne incognita in such amounts as to provide a concentration of 10 ppm. They were mixed uniformly with stirring and then charged into pots each of 1/5000 are. In the charged mixture were sown about 20 seeds of tomato (variety: Kurihara) per pot. The tomato seeds were grown in a greenhouse. Four weeks later, the tomato plants were pulled out so as not to damage their roots. The degree of injury to 10 roots out of them was evaluated on the following ratings, and a root-knot index was calculated.

| Degree of injury | |
|---|---|
| 0 | no root-knot formation (perfect control) |
| 1 | slight root-knot formation |
| 3 | much root-knot formation |
| 4 | greatest root-knot formation (corresponding to non-treatment) |

$$\text{Root-knot index} = \frac{\Sigma(\text{rating} \times \text{number of roots})}{\text{total number of examined roots} \times 4} \times 100$$

From above, the following control effect was obtained:

$$\text{Control effect} = \frac{\left(\begin{array}{c}\text{root-knot index of}\\\text{untreated plot}\end{array}\right) - \left(\begin{array}{c}\text{root-knot index}\\\text{of treated plot}\end{array}\right)}{\text{root-knot index of untreated plot}} \times 100$$

The control effect of 100% means perfect control. The results are shown in Table 8.

TABLE 8

| Compound No. | Concentration of the active ingredient (ppm) | Control effect (%) |
|---|---|---|
| (1) | 10 | 100 |
| (4) | " | 100 |
| (5) | " | 100 |
| (6) | " | 100 |
| (7) | " | 100 |
| (9) | " | 100 |
| (11) | " | 100 |
| Comparison | | |
| IV-1 | 10 | 15 |

It will be appreciated that the instant specification and examples are set forth by way of illustration and not limitation, and that various modifications and changes may be made without departing from the spirit and scope of the present invention.

What is claimed is:

1. An O-alkyl-S-alkyl-S-acyloxyethyl-phorphorodithiolate of the formula

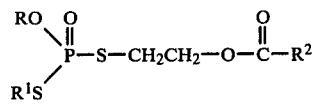

wherein
R is an alkyl group having 1 to 6 carbon atoms,
$R^1$ is an alkyl group having 1 to 6 carbon atoms or an alkoxyethyl group having 1 to 6 carbon atoms in the alkyl part, and
$R^2$ is an alkoxy group having 1 to 6 carbon atoms, an amino group mono- or di-substituted by an alkyl group having 1 to 6 carbon atoms, an unsubstituted anilino group, or an anilino group substituted at the N-position by an alkyl group having 1 to 6 carbon atoms.

2. A method of combating pests which comprises applying to the pests, or to a habitat thereof, a pesticidally effective amount of a compound according to claim 1.

3. The method according to claim 2, wherein such compound is
O-ethyl-S-2-(dimethylcarbamoyloxy)ethyl-S-propyl-phosphorodithiolate,
O-ethyl-S-2-(diethylcarbamoyloxy)ethyl-S-sec-butyl-phosphorodithiolate,
O-ethyl-S-2-(methoxycarbonyloxy)-ethyl-S-2-(ethoxy)-ethyl-phosphorodithiolate, or
O-ethyl-S-2-(diethylcarbamoyloxy)-ethyl-S-2-(ethoxy)-ethyl-phosphorodithiolate.

4. A compound according to claim 1, wherein R is an ethyl group and R¹ is a propyl, sec-butyl or 2-ethoxyethyl group.

5. A compound according to claim 1, wherein such compound is O-ethyl-S-2-(dimethylcarbamoyloxy)ethyl-S-propylphosphorodithiolate of the formula

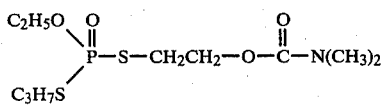

6. A compound according to claim 1, wherein such compound is O-ethyl-S-2(diethylcarbamoyloxy)ethyl-S-sec-butyl-phosphorodithiolate of the formula

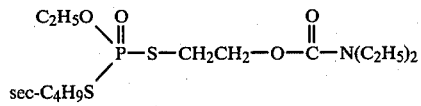

7. A compound according to claim 1, wherein such compound is O-ethyl-S-2-(methoxycarbonyloxy)-ethyl-S-2-(ethoxy)-ethyl-phosphorodithiolate of the formula

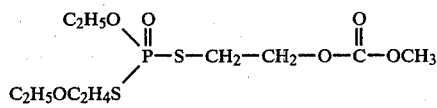

8. A compound according to claim 1, wherein such compound is O-ethyl-S-2-(diethylcarbamoyloxy)-ethyl-S-2-(ethoxy)-ethyl-phosphorodithiolate of the formula

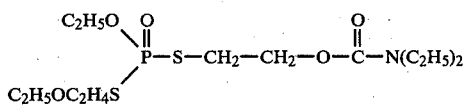

9. A pesticidal composition comprising a pesticidally effective amount of a compound according to claim 1 in admixture with a diluent.

* * * * *